United States Patent [19]

Inbar et al.

[11] Patent Number: 5,314,074
[45] Date of Patent: May 24, 1994

[54] METHOD AND MEANS FOR DENSITY GRADIENT CENTRIFUGATION

[75] Inventors: Michael Inbar, Maskeret Batya; Gerald Slutzky, Jerusalem; Mordechai Radushetzky, Benyamin; David Shitrit, Jerusalem, all of Israel

[73] Assignee: Eldan Technologies Co. Ltd., Jerusalem, Israel

[21] Appl. No.: 971,525

[22] Filed: Nov. 3, 1992

[30] Foreign Application Priority Data

Jan. 31, 1992 [IL] Israel ................................. 100828

[51] Int. Cl.⁵ ............................................ B03D 1/00
[52] U.S. Cl. ..................................... 209/208; 210/516
[58] Field of Search ........................... 494/16, 20, 37; 210/514, 515, 516, 518, 789, 512.1; 209/17, 208, 915, 199

[56] References Cited

U.S. PATENT DOCUMENTS

| | | | |
|---|---|---|---|
| 4,001,122 | 1/1977 | Griffin | 210/789 X |
| 4,083,788 | 4/1978 | Ferrara | 210/516 |
| 4,224,942 | 9/1980 | Wu et al. | 209/208 X |
| 4,257,886 | 3/1981 | Kessler | 210/516 |
| 4,417,981 | 11/1983 | Nugent | 210/516 X |
| 4,492,634 | 1/1985 | Villa-Real | 210/516 X |
| 4,602,995 | 7/1986 | Cassaday et al. | 210/516 X |
| 4,636,361 | 1/1987 | Marián et al. | 210/515 X |
| 4,683,058 | 7/1987 | Lyman et al. | 210/518 X |
| 4,722,792 | 2/1988 | Miyagi et al. | 210/518 X |
| 4,818,386 | 4/1989 | Burns | 210/516 X |
| 4,822,495 | 4/1989 | Michels | 210/514 X |
| 4,824,560 | 4/1989 | Alspector | 209/208 |
| 5,053,134 | 10/1991 | Luderer et al. | 210/516 |

Primary Examiner—D. Glenn Dayoan
Attorney, Agent, or Firm—Helfgott & Karas

[57] ABSTRACT

In the performance of density gradient centrifugation back mixing after centrifugation is prevented by placing a snugly fitted layering insert within the vessel. The insert is capable of supporting the body of liquid dispersion to be centrifuged under regular gravity condition and enables bi-directional cross-flow during centrifugation. A small mesh filter plate may be placed on top of the layering insert.

13 Claims, 1 Drawing Sheet

METHOD AND MEANS FOR DENSITY GRADIENT CENTRIFUGATION

FIELD OF THE INVENTION

The present invention is in the field of density gradient centrifugation. Density gradient centrifugation is a technique used for gravity separation of different solid components of a liquid dispersion such as, for example the separation of red and white blood cells, the purification of biological material such as cell components, viruses, various types of macromolecules, etc.

BACKGROUND OF THE INVENTION AND PRIOR ART

In the performance of density gradient centrifugation, a working fluid is used such as, for example, an aqueous polysaccharide solution commercially available under the trademarks Ficoll-Paque TM or Histo-Paque TM and having a density larger than that of the liquid phase of the dispersion to be centrifuged and intermediate between the densities of the solid components thereof. Preparatory to centrifugation, the liquid dispersion to be centrifuged is layered on top of a working fluid within a centrifugation vessel with as clean an interface between the two as possible, and upon centrifugation there results a liquid column with a density gradient in which, similar as in column chromatography, each of the solid components of the original dispersion occupies a different layer from where it may be separately recovered.

The crucial problem in the performance of density gradient centrifugation is the charging of the centrifugation vessel so as to ensure a clean interface between the lower body of working fluid and the upper body of liquid dispersion. In accordance with the state of the art various manual techniques and skills have been developed to this end. Thus, by one method the dispersion to be centrifuged, for example native or diluted blood, is first placed into the centrifugation vessel and the heavier working fluid is then carefully pipetted underneath the body of fluid to be centrifuged. Alternatively, the working fluid is first filled into the centrifugation vessel and the liquid to be centrifuged is carefully layered thereon.

Obviously both these procedures are tedious, require a high amount of skill and are unsuitable for serial operation.

U.S. Pat. No. 4,824,560 discloses method and means for centrifugation by which a tubular vessel is used with at least two compartments in a row communicating with one another via a narrow, essentially capillary opening. For operation, the working fluid is charged into the lower compartment and the liquid to be centrifuged into the upper one with no need for any special precautions to avoid mixing prior to centrifugation. While this method has some significant advantage over the above-described purely manual methods, it has the drawback that the rather narrow passage between the compartments provides some resistance even during centrifugation which may prolong the operation. Moreover, the method requires specially devised centrifugation vessels which renders it relatively costly. Furthermore, since in accordance with that method the entire lowermost compartment must be filled with working fluid it is not possible to vary the amount of working fluid in a given centrifugation vessel.

It is the object of the present invention to provide an improved method and means for density gradient centrifugation.

SUMMARY OF THE INVENTION

In accordance with the present invention there is provided a method of performing density gradient centrifugation for the recovery of at least one solid matter component from a liquid dispersion, comprising charging a body of working fluid into the lower part and a body of said liquid dispersion into the upper part of a centrifugation vessel, sealing the vessel and subjecting it to centrifugation whereby a density gradient is established, and withdrawing said at least one solid matter component, characterised by the provision within said centrifugation vessel of a snugly fitting layering insert capable of supporting said body of liquid dispersion under regular gravity conditions and of enabling bi-directional cross-flow during centrifugation.

The centrifugation vessel is made of any suitable material that lends itself to sterilization by irradiation or treatment with ethylene oxide, typical examples being glass, plastic material such as polyamide, high density polyethylene, polystyrene, polycarbonate, etc.

In operation the centrifugation vessel is preferably capped or stoppered.

Prior to operation the inside of the centrifugation vessel is preferably rendered sterile, e.g. by exposure to ionizing radiation or by treatment with a sterilizing agent such as ethylene oxide.

The layering insert is designed to fit into an ordinary centrifugation tube.

For operation a body of working fluid is first charged into the bottom portion of a centrifugation vessel whereupon the layering insert is introduced. This is followed by pouring the liquid dispersion to be centrifuged on top of the insert with no need for any precaution in order to avoid mixing. Depending on the nature of the layering insert, some dispersion may slowly sink across onto said body of working fluid without, however, disturbing the surface thereof.

The relative proportions of working fluid and liquid dispersion can be judiciously selected without any lower or upper compartment constraints, which is a significant improvement over the teachings of U.S. Pat. No. 4,824,560. Preferably an anticoagulant is introduced into the upper part of the centrifugation vessel above said layering insert, typical examples being sodium citrate, ethylenediamine-tetraacetic acid (EDTA) and heparin.

The layering insert provided in accordance with the present invention may be in the form of a disk, a cup or an inverted cup and may be made of any suitable material such as, for example, a plastic material, aluminum and the like.

In accordance with one embodiment of the invention the layering insert has a plurality of capillary holes and/or circumferential indentations. Typically the diameter of the capillary holes is within the range of 0.6–0.8 mm and the circumferential indentations have a hemi-circular profile with radii ranging from 0.2 to 0.3 mm.

In accordance with another embodiment of the invention the insert comprises a disk having one or more narrow cuts or lines of weakness whereby the membrane is divided into segments which yield under the action of centrifugal forces. Preferably the said segments revert to the starting configuration when the centrifugation forces cease. The cuts or lines of weakness are, as a rule quite narrow and can be made by scribing with the aid of a sharp tool such as, for example, a razor blade-type scribing or cutting tool.

If desired, a small-mesh filter plate may be super-positioned on the layering insert for better preventing any back-mixing of separated solid matter, which filter plate may, for example, be a cloth woven from synthetic fibers.

If desired, centrifugation vessels holding a given amount of working fluid and fitted with a layering insert according to the invention, may be capped and stored in this form, preferably under sterile conditions. In this way all that is required for centrifugation is to decap the vessel, optionally dilute the working fluid inside the vessel, pour in the desired amount of liquid dispersion, if desired add some anticoagulant, again cap the vessel and subject it to centrifugation.

In accordance with one embodiment of the invention there is used a sterilized vessel fitted with a layering insert and optionally also an overlaying small-mesh filter plate, holding under reduced pressure an amount of working fluid and, if desired, also coagulant and sealed with a member such as a stopper or cap of rubber or the like, capable of holding a vacuum inside the vessel and being penetrable by a needle. Blood for centrifugation can be injected directly from a patient's blood vessel into a so-prepared centrifugation vessel without exposure to the ambient surroundings.

The reduced pressure within the vessel in accordance with the above embodiment is so selected that the required amount of blood is readily sucked in, a typical example being 440 torr (0.58 atm).

It is thus seen that in accordance with the invention there is provided a reliable and versatile method of density gradient centrifugation suitable for serial operation.

Upon completion of the centrifugation according to the invention, light fractions accumulating above the layering insert may be withdrawn in any suitable way, e.g. by aspiration with a pipette or by decantation. If desired, the sediment accumulating underneath the layering insert can also be recovered in any suitable way.

The invention further provides an insert of the kind specified for use in centrifugation.

Still further, the invention provides a centrifugation vessel holding a body of working fluid underneath a snugly fitting insert dividing the tube into upper and lower compartments. If desired, a small mesh filter plate is provided on top of the layering insert.

In accordance with one embodiment, the above centrifugation vessel is evacuated and sealed with a stopper or cap of rubber or the like, capable of holding the vacuum inside the vessel and being penetrable by a needle.

DESCRIPTION OF THE DRAWINGS

For better understanding the invention will now be described, by way of example only, with reference to the annexed drawings in which.

DESCRIPTION OF SPECIFIC EMBODIMENTS

Figure 1:
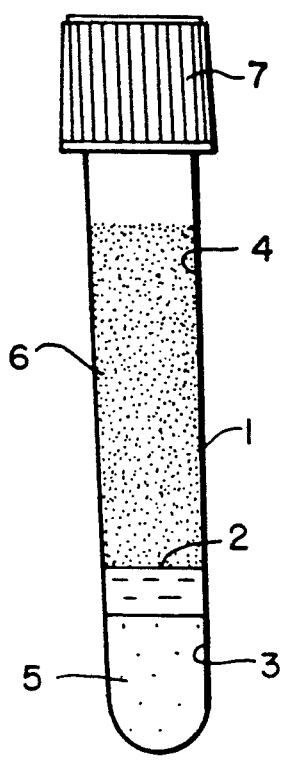
FIG. 1 shows a capped centrifugation tube with a layering insert according to the invention, prior to centrifugation.

As shown in FIG. 1, a centrifugation tube 1 holds a snugly fitting layering insert 2 dividing the tube into a lower compartment 3 and an upper compartment 4 holding respectively, a body of working liquid 5 and a body of a liquid dispersion to be centrifuged 6, e.g. native or diluted blood. The layering insert 2 has openings of a capillary nature which ensures that regardless of the manner in which the liquid dispersion is poured on top of insert 2, any penetration of the lowermost part of the dispersion body 6 into compartment 3 occurs only very gently and in a way that does not disturb the surface of the body of the working fluid 5. The tube is capped by means of a suitable cap 7, e.g. of rubber.

In the course of centrifugation there occurs a bi-directional flow of liquid across insert 2 between the upper and lower compartments 3 and 4 and at the end of centrifugation there forms a continuous density gradient with the white blood cells forming an upper layer 8 and the red blood cells forming a sediment 9. The white blood cells 8 may be removed by aspiration with a pipette or by decantation and the sediment of red blood cells may either also be removed by aspiration with a pipette adapted to penetrate through one of the holes in the layering insert 2, or else the insert may first be withdrawn by means of a suitable tool and the red blood cells are then sucked out or decanted.

Figure 3:
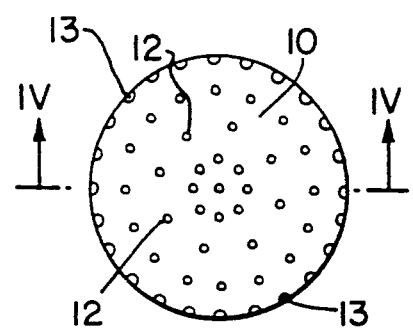
FIG. 3 is a plan view of one embodiment of an insert according to the invention.
Figure 4:
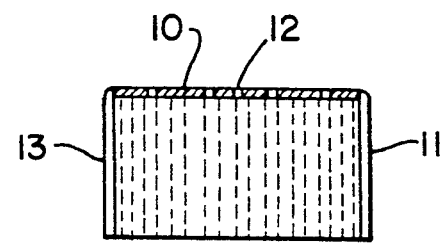
FIG. 4 is a section along line IV—IV of FIG. 3.

A first embodiment of a layering insert 2 according to the invention is shown in FIGS. 3 and 4. As shown, the insert, which may be of plastic material, has the shape of an inverted cup comprising a circular disk 10 and a skirt 11. Disk 10 has a plurality of capillary size holes 12 and skirt 11 is serrated by a plurality of axial indentations or grooves 13. The layering insert is designed to fit snugly into a centrifugation tube and is held in position by friction.

For operation, a desired quantity of working liquid 5, e.g. Ficoll-Paque TM, is first charged into a tube 1 which is followed by the insertion of the layering insert 2, preferably with the skirt down as shown in FIG. 4. Centrifugation tubes with working liquid and each holding a layering insert 2, may be stored, if desired under sterile conditions, until needed or else be used right away. For use, the liquid dispersion to be centrifuged, e.g. blood, is poured onto the layering insert 2 with no need for any precautionary measures, following which the tube is capped and ready for centrifugation.

The embodiment of the layering insert according to the invention shown in FIGS. 5 and 6 is again in the shape of an inverted cup. It comprises a disk 15 with a depending skirt 16 and has two narrow cuts 17 and 18 dividing the disk into four equal segments 19. Skirt 16 is smooth with no indentations or grooves.

The sequence of operations is similar as with the embodiment of FIGS. 3 and 4. The physical properties of the cut disk 15 are so selected that it readily supports the body 6 of liquid dispersion to be centrifuged under regular gravity conditions while upon centrifugation the increased gravity field causes all four disk segments 19 to collapse partially and thereby be separated from one another, whereby free passage for bi-directional flow between the upper and lower compartments 3 and 4 is provided. At the end of the operation segments 19 may revert to their starting position.

It is thus seen that in accordance with the invention the problem of clean layering for the purpose of density gradient centrifugation is solved in a simple and reliable manner suitable for serial operation. In the initial, pre-centrifugation stage, a layering insert according to the invention, whether according to FIGS. 3 and 4 or FIGS. 5 and 6, prevents leakage of working fluid from the bottom of the centrifugation vessel during routine operations of storage and handling, without any preliminary centrifugation or other treatment being required.

Figure 5:
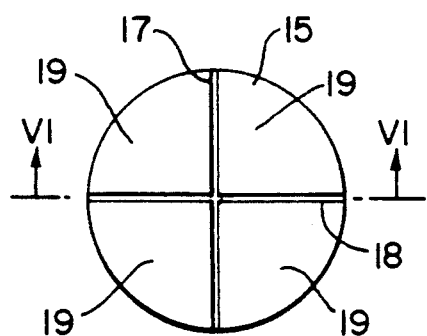
FIG. 5 is a plan view of another embodiment of an insert according to the invention.
Figure 7:
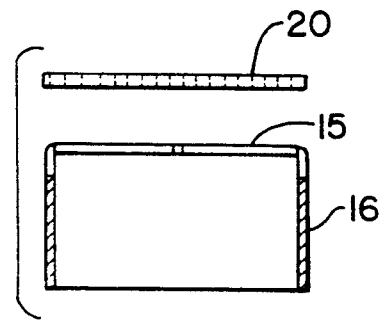
FIG. 7 is an exploded view of a modification of the insert according to FIGS. 5 and 6.
Figure 6:
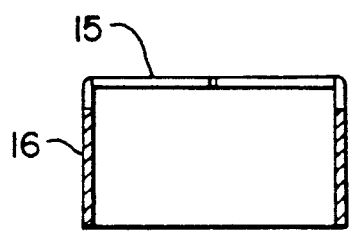
FIG. 6 is a section along line VI—VI of FIG. 5.

A modification of the embodiment of FIGS. 5 and 6 is shown in FIG. 7 in exploded fashion. As shown, a small mesh round filter plate 20 is super-positioned on the layering insert 15, 16, serving for the prevention of any back mixing of separated solid matter at the end of the centrifugation which, when the supernatant liquid phase is poured out, might otherwise pass across plate 15 in case the segments 19 do not fully revert to their starting position. Filter plate 20 can be made of cloth woven from synethetic fibers, e.g. polyethylene or polypropylene. For example, a double woven polypropylene fiber cloth obtained from Swiss Silt Bolting Cloth Mfg. Co. of Zurich under the trade name Tetex TM, may be used. The mesh of such a filter plate may have pores of 20–120μ in diameter and the fabric is typically 860–1280μ thick.

The following working example illustrates the manner in which the invention operates.

EXAMPLE

The cap is removed from a plastic centrifugation tube (approximately 16×100 mm) and a plastic insert of the kind shown in FIGS. 5 and 6, is inserted. The insert has a diameter of 12 mm and skirt 16 is 8 mm high. The insert is so introduced that the circular disk 15 is uppermost and disk 15 is then covered by a small mesh round filter plate such as shown in FIG. 7. 2 ml of Ficoll-Plaque TM is introduced as working fluid which is an aqueous solution containing 5.6% w/w of polysucrose, 9.6% w/w of sodium metrizoate having a density of 1.077 g/l and an osmolality of 280 mOsm. The insert and filter plate are so placed that the skirt 16 will rest slightly above the surface of the working fluid. The tube is then capped and exposed to ionizing radiation in order to render the inside of the tube sterile. The tube is then opened under sterile conditions, 2 ml of sterile Ficoll-Paque TM are added, and the tube is capped again. The tube is briefly centrifuged to displace the Ficoll-Paque TM to the bottom of the tube. This completes the manufacturing phase.

The sterile tube with working fluid and layering insert is first diluted by a 1:1 or 1:2 ratio with sterile saline or other sterile isotonic solution. A volume of the diluted blood, appropriate to the volume of Ficoll-Paque TM and the size of the tube, is poured directly into the tube onto the layering insert with no special precaution and the blood will remain entirely on top of the insert and overlaying filter plate and will come in contact with the Ficoll layer only during the centrifugation step. At this time the conditions within the tube are as shown schematically in FIG. 1.

If, instead of the insert of FIGS. 5 and 6, one according to FIGS. 3 and 4 is used, some of the blood will pass across the insert in a gentle flow and form a layer on top of the working fluid without, however, disturbing the surface thereof.

Figure 2:
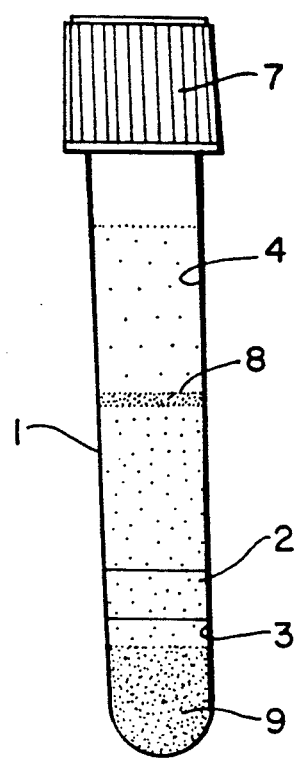
FIG. 2 shows the same tube after centrifugation.

The tube is now placed into a clinical centrifuge for 10 min. at approximately 1000×g at room temperature. As the layering insert permits a bi-directional free movement of both the Ficoll and the blood components through the holes 12 and grooves 13 of the layering insert, a gradient is formed that results in the state depicted schematically in FIG. 2. The mononuclear cells appear as a white band 8 between the plasma and the top of the layering insert. The erythrocytes and polymorphonuclear cells will have sedimented through the Ficoll-Paque TM to the bottom of the tube forming sediment 9. The holes 12 in the top of the insert and the circumferential indentations 13 promote both the formation of the gradient and the sedimentation of the red cells. The entire upper liquid phase may be poured out, as the layering insert prevents re-mixing of the erythrocytes. If it is necessary to avoid re-dilution of the white cell layer, the platelet-rich plasma may first be removed by aspiration without disturbing the interface and the circular band 8 of cells is then withdrawn by means of a Pasteur pipette or other suitable device.

We claim:

1. A method of performing density gradient centrifugation for the recovery of at least one solid matter component from a liquid dispersion, comprising providing a centrifugation vessel having a lower part and an upper part, charging a body of working fluid into the lower part and a body of said liquid dispersion into the upper part of the centrifugation vessel, sealing the vessel and subjecting it to centrifugation whereby a density gradient is established, and withdrawing said at least one solid matter component, wherein a snugly fitting layering insert is provided within said centrifugation vessel for supporting said body of liquid dispersion under regular gravity conditions and enabling bi-directional cross-flow during centrifugation, and wherein the insert comprises a disk having one or more narrow cuts or lines of weakness whereby the disk is divided into segments which yield under the action of centrifugal forces.

2. A method according to claim 1, wherein the layering insert has a plurality of capillary holes and circumferential indentations.

3. A method according to claim 1, wherein said segments return to the starting configuration when the centrifugation forces cease.

4. A method according to claim 1, wherein a small mesh filter plate is super-positioned on said layering insert.

5. A method according to claim 1, wherein the layering insert has a plurality of capillary holes.

6. A method according to claim 1, wherein the layering insert has a plurality of circumferential indentations.

7. A layering insert for use in density gradient centrifugation, which layering insert fits snugly into a centrifugation vessel for supporting a body of liquid dispersion inside said centrifugation vessel under regular gravity conditions and enables bi-direction cross-flow during centrifugation, the insert comprising a disk having one or more narrow cuts or lines of weakness whereby the disk is divided into segments which yield and collapse under the action of centrifugal forces.

8. A layering insert according to claim 7, having of a plurality holes and of circumferential indentations.

9. A layering insert according to claim 7, having a plurality of holes.

10. A layering insert according to claim 7, having a plurality of circumferential indentations.

11. A centrifugation vessel comprising a layering insert and holding a body of working fluid underneath the layering insert, said layering insert being fitted snugly into the centrifugation vessel for supporting a body of liquid dispersion inside said centrifugation vessel under regular gravity conditions and enabling bi-direction cross-flow during centrifugation, and a small mesh filter plate super-positioned on said layering insert.

12. A centrifugation vessel according to claim 11, and further comprising a sealing member for evacuating and sealing the centrifugation vessel, said sealing member being capable of holding a vacuum inside the vessel and penetrable by a needle.

13. A centrifugation vessel according to claim 12 also including a small mesh filter plate super-positioned on said layering insert.

* * * * *